United States Patent [19]

Gregory

[11] Patent Number: 5,354,324
[45] Date of Patent: Oct. 11, 1994

[54] LASER INDUCED PLATELET INHIBITION

[75] Inventor: Kenton W. Gregory, Boston, Mass.

[73] Assignee: The General Hospital Corporation, Boston, Mass.

[21] Appl. No.: 600,014

[22] Filed: Oct. 18, 1990

[51] Int. Cl.⁵ ............................................. A61N 5/00
[52] U.S. Cl. ...................................... 607/92; 607/89; 607/93; 606/14
[58] Field of Search ................................ 128/395–398, 128/662.06, 786, 6; 606/194, 15, 3, 7, 159; 604/95; 350/46.34, 96 R, 96.29

[56] References Cited

U.S. PATENT DOCUMENTS

| | | | |
|---|---|---|---|
| 3,740,113 | 6/1973 | Cass et al. | 350/96 R |
| 3,819,250 | 6/1974 | Kibler | 350/96 R |
| 3,995,934 | 12/1976 | Nath | 350/96 R |
| 4,009,382 | 2/1977 | Nath | 350/96 R |
| 4,045,119 | 8/1977 | Eastgate | 350/96 R |
| 4,201,446 | 5/1980 | Geddes et al. | 350/96.29 |
| 4,207,874 | 6/1980 | Choy | 128/6 |
| 4,373,768 | 2/1983 | Clarke | 350/96.34 |
| 4,505,542 | 3/1985 | Clarke | 350/96.34 |
| 4,556,057 | 12/1985 | Hiruma et al. | |
| 4,747,662 | 5/1988 | Fitz | 350/96.34 |
| 4,799,479 | 1/1989 | Spears | 606/7 |
| 4,829,262 | 5/1989 | Furumoto | |
| 4,848,336 | 7/1989 | Fox et al. | 606/7 |
| 4,870,953 | 10/1989 | DonMicheal et al. | 606/159 |
| 4,966,596 | 10/1990 | Kuntz et al. | 606/7 |
| 5,019,075 | 5/1991 | Spears et al. | |
| 5,040,548 | 8/1991 | Yock et al. | 128/898 |
| 5,053,033 | 10/1991 | Clarke | 606/15 |
| 5,092,841 | 3/1992 | Spears | 606/194 |

FOREIGN PATENT DOCUMENTS

US9107627 2/1992 PCT Int'l Appl.

OTHER PUBLICATIONS

Epstein, *Circulation,* 1989, 80:757.

Primary Examiner—Mark S. Graham
Attorney, Agent, or Firm—Stetina and Brunda

[57] ABSTRACT

A method for preventing platelet adhesion to a vascular surface in a mammal, which includes irradiating the vascular surface with a pulse of laser energy having a pulse duration less than the thermal relaxation time of the irradiated vascular surface, wherein lasar energy is delivered to said vascular surface via radiographic contrast material.

35 Claims, No Drawings

LASER INDUCED PLATELET INHIBITION

This invention was made with Government support under Contract N00014-86-K-0117 awarded by the Office of Naval Research. The Government has certain rights in this invention.

BACKGROUND OF THE INVENTION

This invention relates to laser treatment of vasculature.

Platelets play an important role in treatment strategies for coronary arteries thrombi as well as arterial thrombosis in other portions of the body. Coronary artery re-occlusion following fibrinolysis is often due to platelet-rich thrombi in experimental models (Yasuda, J. Amer. Coil. Cardiology, 1989) and can be prevented by administration of monoclonal anti-platelet antibodies (specific for GP11b/111a) (Gold, Circulation, 1989).

Lasers have been employed as heating sources for metal probes in non-selective ablation of thrombus. Continuous wave blue-green argon ion laser irradiation has been used for selective ablation of thrombus, but the long exposure times inherent with this approach frequently result in damaging vessel walls by heat conduction. Some treatment strategies aimed at platelets, e.g., anticoagulation, or thrombolytic therapy (e.g., administration of t-PA), result in severe bleeding complications.

SUMMARY OF THE INVENTION

We have discovered that short-duration pulses of laser irradiation can be used to preferentially treat vascular surfaces, with reduced likelihood of damage to surrounding endovascular tissue, so as to inhibit platelets from adhering or aggregating locally, while not affecting systemic anticoagulation.

In general, in one aspect, the invention features a method for inhibiting platelet adhesion to a surface of the vasculature in a mammal, which includes irradiating the surface with a laser energy pulse having a pulse duration less than the thermal relaxation time of the irradiated surface, wherein the lasar energy is delivered to the vascular surface via radiographic contrast material. As used herein, "surface" of a vessel refers to the internal surface, i.e., facing the lumen; "radiographic contrast material" refers to a fluid which is transparent to optical wavelengths but opaque to xray irradiation and is injected to opacify blood vessels during xray procedures.

In preferred embodiments, the vascular surface may be an arterial surface or a venous surface; the pulse duration is less than one-half, more preferably less than one-tenth, the thermal relaxation time of the irradiated arterial surface. Preferably, the laser energy is delivered to the artery via a fluid-core laser catheter; more preferably, the radiographic contrast material is delivered through the fluid core laser catheter. Preferably, the radiographic contrast material is mixed with a therapeutic amount of one or more anticoagulants, such as heparin, a thrombolytic agent, e.g., one or both of streptokinase or TPA, or a thrombin inhibitor, e.g., argatropin or hirudin. Preferably, the pulse duration is less than 100 $\mu$sec, more preferably less than 2 $\mu$sec, still more preferably about 1 $\mu$sec or less; the pulse can be generated by a flashlamp-excited dye laser; the surface is irradiated with a succession of laser energy pulses, each having a pulse duration less than the thermal relaxation time of the irradiated surface; the repetition rate of the succession of pulses is less than 100 Hz, more preferably about 20 Hz or less, and preferably not greater than the reciprocal of the thermal relaxation time of the irradiated surface; the relaxation interval between successive pulses is greater than 100 $\mu$sec, more preferably greater than one msec, and still more preferably greater than twice the thermal relaxation time of the irradiated surface.

The method may further include administering a therapeutic amount of a thrombolytic agent to the mammal intravenously, intra-arterially, or through the optical fluid stream.

In various aspects, the method is a method for preventing platelet adhesion to an arterial surface following injury to the arterial surface, particularly following occlusion of the artery by a thrombus; or following angioplasty, unstable angina, or acute myocardial infarction.

A "platelet-containing mass", as used herein, is a mass containing platelets, e.g., a layer of platelets covering the vessel surface, or a clot containing platelets, e.g., a thrombus. A thrombus originates at a site of blockage and is a clot or aggregation of blood factors, primarily platelets and fibrin, with the entrapment of cellular elements. A thrombus can originate in a vein or an artery; such a thrombus can break apart, and fragments of it can move away from the place of origin and become lodged elsewhere in the cardiovascular system as an arterial or venous embolus, forming an obstruction which can include foreign material other than a clot. An embolus which dislodges and travels to the lungs can form a pulmonary embolism.

When the arterial surface is irradiated with laser energy, as for example when laser energy is directed at the inner surface of the artery in the form of a beam, the energy is absorbed by various components of the irradiated portion of the arterial surface as the beam penetrates into the artery, and the energy of the beam is progressively attenuated at greater depths beyond the irradiated surface.

For a circular beam consisting of substantially parallel rays, the irradiated portion of the arterial surface has approximately the form of a cylinder whose axis corresponds to the axis of the beam. For purposes of description, the "irradiated volume" of the irradiated surface is taken as a cylinder whose diameter is the diameter of the beam and whose height is the depth to which 67% of the energy of the beam has been absorbed.

As the beam energy is absorbed, heat is generated, and the temperature of the irradiated portion of the arterial surface rises. Heat dissipates away from the irradiated portion of the surface into the cooler matter surrounding it, raising the temperature of the surrounding matter, from which also the heat dissipates. When the beam is shut off or is moved away from the irradiated portion of the arterial surface, the dissipation of heat continues as the temperature of the irradiated arterial surface falls and the irradiated surface and the surrounding matter approach an equilibrium state.

The rate of dissipation of heat for a particular material varies according to the thermal diffusion constant of the material, expressed as K, and the time required for the temperature of the irradiated mass to fall to a specified temperature depends upon K and upon the dimensions of the arterial surface.

The "thermal relaxation time", expressed as t, is the time required for the temperature at an irradiated surface whose temperature has been increased to $T + \Delta T$ by a pulse of energy to return to a temperature $T+0.5(\Delta T)$. The thermal relaxation time t is measured from the initiation of the pulse.

The thermal relaxation time t can be measured directly by the use of, for example, a suitable temperature measuring device; or t can be calculated from a knowledge of the dimensions and thermal characteristics of the irradiated surface. For a uniform surface of small dimensions and for pulses of light energy of short duration, t is related to K and the dimensions of the surface approximately according to the relation $$t = d^2/2K,$$

where d, expressed in cm, is the smaller of: (1) the diameter of the irradiated volume (taken here to be the diameter of the beam, as described above; conventionally expressed as "D"), or (2) the depth of the irradiated volume (taken here as the depth beyond the surface of the irradiated tissue at which 67% of the incident energy has been absorbed; conventionally expressed as "d"). The thermal diffusion constant for most soft tissues and for platelet-containing masses approximates that of water; that is, K is approximately 0.0013 $cm^2/sec$.

The above method of calculating t is given for illustration only; where reference is made to the relationship between pulse duration and t, it is the actual thermal relaxation time of the particular tissue that is intended.

A laser energy "pulse", as that term is used here, means a quantity of laser energy, delivered during a time interval in which the rate of energy delivery is high enough that the energy fluency of the pulse [can cause ablation of the mass,] followed by a time interval in which the rate of energy delivery is low enough to permit thermal relaxation of the surface.

It will be appreciated that the process of diffusion of heat away from the irradiated surface into surrounding matter begins at the moment the temperature of the irradiated surface begins to elevate. Where the pulse duration is sufficiently low with respect to the thermal relaxation time of the irradiated surface, an energy fluence can be directed onto the irradiated surface that is sufficient to alter the character of the surface of the vessel such that platelet adherence is inhibited, yet not so great as to damage surrounding tissues either by direct irradiation or by excessive conductive heating during the relaxation interval.

The "pulse duration" (here expressed in $\mu sec$) of a laser energy pulse is the time interval in which the intensity of the radiation is equal to or greater than half its maximum over the entire pulse. The energy fluence delivered (expressed in $J/cm^2$) by each pulse describes the concentration of energy, or energy per unit area, delivered to the irradiated field.

Where the pulse duration is sufficiently low in comparison to the repetition rate, an interval between pulses occurs, in which the temperature of the irradiated tissue falls as the heat generated during the pulse dissipates into the surrounding matter. The "relaxation interval", as that term is used here, is defined as the difference between the time interval between initiations of succeeding pulses and the pulse duration.

The arterial surface can be irradiated with a series of repeating pulses, and the "repetition rate", as that term is used here, is the rate (expressed in cycles/sec, or Hz) at which pulses are initiated.

The method of the invention provides for the treatment of vascular surfaces with reduced likelihood of damage to surrounding tissues, to prevent platelets from adhering and aggregating locally, while not affecting systemic anticoagulation; that is, with a greater margin of safety to the mammal being treated. The preferential absorption of laser energy by the arterial surface in comparison to surrounding tissues is sufficiently high throughout the visible spectrum that the method can be practiced at wavelengths other than those where absorption maxima occurs. A particular wavelength can be selected to optimize wavelength dependent criteria, including apparatus-related criteria such as ease of transmission through optical fibers and availability, cost and reliability of various laser systems, and including treatment-related criteria such as the desired depth of ablation per pulse.

The method may be combined with other known techniques. For example, pulsed laser irradiation can be used according to the invention to treat vascular surfaces, and in conjunction with (i.e., concurrently or thereafter the vascular surface can be exposed to) one or more thrombolytic agents such as streptokinase or t-PA. The partial breakdown of the obstruction, and the resulting increase in its surface area, can render it more susceptible to the action of the thrombolytic agent. Alternatively, if the patient has been treated with streptokinase or TPA and failed to respond, the method of the invention could be used to treat the thrombus or platelet covered surface by removing the thrombus or platelets. In fact, streptokinase or TPA do not remove the platelet portion of the thrombus; these agents only remove the fibrin portion of the clot; platelets remaining after streptokinase or TPA treatment are available to form another clot, as well as capable of promoting artheriosclerosis by releasing growth factors.

Other features and advantages of the invention will be apparent from the following description of the preferred embodiments thereof and from the claims.

DESCRIPTION OF THE PREFERRED EMBODIMENTS

Any of a variety of practical considerations can enter into the selection or design of delivery catheters and the choice of laser exposure parameters, including wavelength, pulse duration, relaxation interval, and energy fluence. Consideration can be given, for example, to achieving uniform exposure of the arterial surface to laser irradiation; to generate a minimum of debris; to minimize thermal injury to normal structures; and to prevent or reduce the likelihood of vascular perforation.

Any laser which can deliver pulses of the desired intensity, duration, and wavelength can be used. A preferred laser is a flashlamp-excited pulsed dye laser (Dymed pulsed dye laser Model 3000). Lasar energy is delivered to the vessel surface via radiographic contrast material; any standard contrast material may be used, e.g., angiovist (Berlex, Wayne, N.J.) or hexabrix (Mallincrodt, St. Louis, Mo.). The fiber optic bundles and auxiliary apparatus by which laser light is delivered to the obstruction can be of any conventional configuration, for example, as described in Choy, U.S. Pat. No. 4,207,874. A second fiber optic bundle can be used for detecting an obstruction, if one exists, and monitoring the progress of ablation of the obstruction.

The fluence ($Joules/cm^2$) of the laser light should be sufficiently high to treat the arterial surface at the wavelength and pulse duration employed, and not so high as to cause unacceptable damage to surrounding healthy tissue. The requisite fluence range varies with the diameter of the optical fiber used, with smaller diameter fibers requiring higher fluences to compensate for scattering losses at the periphery of the illuminated volume.

Procedure

The method of the invention can be used for selectively treating vascular surfaces to prevent platelets from adhering and aggregating locally in vivo by employing known methods of directing optical energy to irradiate the vascular surface with laser energy having suitable pulse duration, as described generally above.

Example

An animal model of coronary artery thrombosis (developed by Herman Gold and Louise Guerrero, Massachusetts General Hospital) was used to test the method of the invention. In this model, the animal is under anesthesia and the left circumflex or left anterior descending coronary artery is treated. First, the artery is isolated and an external hose clamp plastic connector is placed around the distal coronary artery. Arterial blood flow is decreased with the clamp to reduce flow by 50%, which corresponds to a 90 stenosis. The proximal artery is then damaged by forcep compression, thus effectively removing the endothelium and results in deep tears to the media. A period of 20 min. of perfusion is allowed for platelet adhesion and aggregation and then thrombin in whole blood is injected in a proximal side branch to create a mixed platelet and fibrin thrombus. The thrombus is allowed to mature for 3 hours before laser treatment is accomplished.

Materials

Laser energy deposition is performed with a Dymed pulse dye laser or a candela pulse dye laser (Candela Corp., Wayland, Mass.) emitting light pulses. This laser generated 1 $\mu$sec-long pulses at a repetition rate of 3-5 hertz. Approximately 3-10 joules/cm$^2$ is used in a 1 mm$^2$ irradiation area. Laser output spectrum was measured with a monochromator, and ranged from 480 to 580 nm with the maximum at 482 nm. Pulse width was measured with a reverse biased silicon photodiode (EG&G, Salem, Mass.). The laser radiation was focused with a 2.5 cm focal length quartz lens into a 320 $\mu$m core diameter quartz optical fiber (Spectran Corp., Sturbridge, Mass.). The delivered energy per pulse was measured with an energy meter (Scientech, Boulder, Colo.) or a power meter (Coherent, Palo Alto, Calif.), and varied ±5%. Approximately 100-1000 laser pulses are needed in this experimental model.

The laser energy is delivered to the circumflex or left anterior descending coronary arteries via a fluid core laser catheter. The fluid core laser catheter is introduced into the coronary artery with conventional angioplasty guidewire and guiding catheter techniques. A power injector is connected to the fluid core catheter and radiographic contrast media is injected to carry the light to the coronary artery under fluoroscopic guidance.

Results

The method of the invention was tested by performing the above-described animal test on 22 dogs. The left anterior descending or left circumflex coronary artery in each dog was damaged by forcep compression and a mixed platelet and fibrin thrombus allowed to form before the artery was exposed to laser irradiation. All 22 arteries achieved reprofusion; of these, 2 became reoccluded within 30 min. and 2 demonstrated cyclic reocclusion; the remaining 18 remained patent for a mean of 1.4 hr. Thus, the method of the invention gives an 80% patency rate. Four control arteries which did not receive laser treatment also did not achieve reperfusion and were occluded at the time of evaluation. Compared to arteries treated with recombinant TPA, which show a 20% patency rate at 10 min., the above-irradiated arteries show an 80% patency rate at a mean of 1.4 hr.

Histology and Electron Microscopy

Fresh specimens of coronary artery were obtained from the above-described test dogs. The specimens were processed for routine histology with hematoxylin and eosin staining.

Histologic evaluation of coronary arteries which had been previously occluded and laser treated to remove platelets and fibrin revealed a widely patent artery in a tract through which the fiber passed. There was no evidence of carbonization or thermal alteration of either the embolus or the underlying coronary artery. A high power magnification of one artery showed a clean arterial surface with no platelet deposition. Histologic evaluation of an artery which was comparatively treated with T-PA showed a patent artery at 7½ min. and the absence of subendothelial structures. However, deep layers of platelets and fibrin were evident with platelet monolayers as well as aggregates.

The specimens were also processed for scanning electron microscopy of the laser irradiated arteries which showed deep medial tears resulting from forceps denudation, but no platelet deposition. Laser-treated surfaces were notable in that they showed either the complete absence of adhering platelets or a markedly reduction in platelet adherence compared to control dogs or dogs treated with TPA or streptokinase. A transmission electron micrograph of a laser treated vessel following forceps trauma revealed dead and dying smooth muscle cells, no endothelial cells, no internal elastic lumen, and no base membrane. Undenatured collagen fibrils were covered by an electron dense layer which might prevent platelets from recognizing collagen receptors and, thus, inhibit platelet adhesion.

Use

Pulsed laser radiation can be employed with a wide margin of safety to a previously occluded vessel to prevent reocclusion, or to a vessel that is sub-occluded by platelet or thrombus adherence. A wide range of wavelengths may be used to treat the vessel surface; wavelength-dependent criteria which may be considered are depth of optical penetration, desired depth of ablation per laser pulse, ease of transmission through optical fibers, and cost and reliability of various laser systems.

The method of the invention may also be used for canalization, disruption, or ablation of a platelet-containing mass; e.g., for treatment of acute and chronic coronary artery thrombotic syndromes, as well as arterial thrombosis in other organs; for treatment of acute myocardial infarction; for prevention of thrombosis and restenosis following enterectomy or balloon angioplasty; and for treatment of unstable angina. Laser irradiation can advantageously be combined for example with infusion, according to conventional techniques, of a thrombolytic agent such as streptokinase or t-PA for safe and efficient removal of a mass.

The inventive method can also be used for the selective ablation of thrombus and prevention of reocclusion in a graft of the kind used, for example, in bypass surgery for diverting blood around blockages in the arterial systems. The invention can be used in tissue grafts or in grafts made from a prosthetic material, and the pulse widths and energy fluencies can be adjusted to provide efficient treatment of the arterial surface without damaging the graft.

Other embodiments are within the following claims.

I claim:

1. A method for inhibiting platelet adhesion to a mammalian blood vessel surface having a known thermal relaxation time, said method comprising the steps of:
   a. inserting, into a blood vessel, an elongate liquid core laser catheter having a liquid carrying lumen extending longitudinally therethrough such that a flow of laser transmitting liquid may be infused through said catheter;
   b. passing a laser transmitting liquid through the liquid carrying lumen of said catheter such that said liquid passes through said catheter and into contact with said blood vessel surface;
   c. causing a pulse of laser energy to be transmitted into said liquid passing through the lumen of said catheter such that said liquid will carry said laser energy into contact with said blood vessel wall, thereby causing irradiation of said blood vessel wall; and
   d. maintaining the pulse duration of said pulse of laser energy such that the elapsed time from the beginning of said pulse to the end of said pulse is less than the thermal relaxation time of the irradiated blood vessel surface.

2. The method of claim 1 wherein said blood vessel surface is arterial.

3. The method of claim 1 wherein said blood vessel surface is venous.

4. The method of claim 2 or 3 wherein said laser energy is administered to said surface following injury to said surface.

5. The method of claim 4 wherein said injury includes a platelet-containing mass and said laser energy irradiation is applied to an area of said surface surrounding said platelet containing mass.

6. The method of claim 5 wherein said mass comprises a layer of platelets.

7. The method of claim 2 wherein said laser energy is administered to said arterial surface following angioplasty.

8. The method of claim 1 wherein said pulse duration is less than one-half of the thermal relaxation time of the blood vessel surface to which said laser energy is directed.

9. The method of claim 1 wherein said pulse duration is less than one-tenth said thermal relaxation time.

10. The method of claim 1 wherein said pulse duration is less than 100 μsec.

11. The method of claim 1 wherein said pulse duration is less than 2 μsec.

12. The method of claim 1 wherein said pulse duration is less than about 1 μsec.

13. The method of claim 2, further comprising irradiating said arterial surface with a succession of pulses of laser energy, each having a pulse duration less than the thermal relaxation time of the irradiated surface.

14. The method of claim 13 wherein the repetition rate of said succession of pulses is less than the reciprocal of the thermal relaxation time of the irradiated blood vessel surface.

15. The method of claim 13 wherein the repetition rate of said succession of pulses is less than 100 Hz.

16. The method of claim 13 wherein the repetition rate of said succession of pulses is less than about 20 Hz.

17. The method of claim 13 wherein the relaxation interval between said successive pulses is greater than 1 msec.

18. The method of claim 13 wherein the relaxation interval between successive said pulses is greater than about 100 μsec.

19. The method of claim 1 wherein said laser transmitting liquid is mixed with one or more anticoagulants.

20. The method of claim 19, said one or more anticoagulants being heparin, a thrombolytic agent, or a thrombin inhibitor.

21. The method of claim 20 wherein said at least one anticoagulant consists of a thrombolytic agent selected from the group consisting of:
   i. streptokinase;
   ii. tissue plasminogen activator; and
   iii. the combination of streptokinase and tissue plasminogen activator.

22. The method of claim 1 or 13 wherein said pulse of laser energy is generated by a flashlamp-excited dye laser.

23. The method of claim 1, further comprising the step of:
   (e) administering to said mammal in conjunction with said laser irradiation of said blood vessel surface, a therapeutic amount of a thrombolytic agent.

24. The method of claim 5 wherein said mass comprises a thrombus.

25. The method of claim 1 wherein said laser transmitting liquid comprises a radiographic contrast medium.

26. The method of claim 25 wherein said radiographic contrast medium is selected from the group of commercially available radiographic contrast media consisting of:
   Angiovist (Berlex, Wayne, N.J.); and
   Hexabrix (Mallincrodt, St. Louis, Mo.).

27. A method for treating at least one artery involved in acute myocardial infarction wherein said artery has a known thermal relaxation time, said method comprising the steps of:
   a. inserting, into said artery, an elongate liquid core laser catheter having a liquid carrying lumen extending longitudinally therethrough such that a flow of laser transmitting liquid may be infused through said catheter;
   b. passing a laser transmitting liquid through the liquid carrying lumen of said catheter such that said liquid passes through said catheter and into contact with a surface of said artery;
   c. causing a pulse of laser energy to be transmitted into said liquid passing through the lumen of said catheter such that said liquid will carry said laser energy into contact with said artery surface, thereby causing irradiation of said artery surface; and
   d. maintaining the pulse duration of said pulse of laser energy such that the elapsed time from the beginning of said pulse to the end of said pulse is less than the thermal relaxation time of the irradiated artery surface.

28. The method of claim 21 wherein said laser transmitting liquid comprises a radiographic contrast medium.

29. A method for treating at least one artery involved in unstable angina wherein said artery has a known thermal relaxation time, said method comprising the steps of:
 a. inserting, into said artery, an elongate liquid core laser catheter having a liquid carrying lumen extending longitudinally therethrough such that a flow of laser transmitting liquid may be infused through said catheter;
 b. passing a laser transmitting liquid through the liquid carrying lumen of said catheter such that said liquid passes through said catheter and into contact with a surface of said artery;
 c. causing a pulse of laser energy to be transmitted into said liquid passing through the lumen of said catheter such that said liquid will carry said laser energy into contact with said artery surfaces, thereby causing irradiation of said artery surface; and,
 d. maintaining the pulse duration of said pulse of laser energy such that the elapsed time from the beginning of said pulse to the end of said pulse is less than the thermal relaxation time of the irradiated artery surface.

30. The method of claim 29 wherein said laser transmitting liquid comprises a radiographic contrast medium.

31. A method for preventing arterial occlusion following balloon angioplasty wherein said artery has a known thermal relaxation time, said method comprising the steps of:
 a. inserting, into said artery, an elongate liquid core laser catheter having a liquid carrying lumen extending longitudinally therethrough such that a flow of laser transmitting liquid may be infused through said catheter;
 b. passing a laser transmitting liquid through the liquid carrying lumen of said catheter such that said liquid passes through said catheter and into contact with a surface of said artery;
 c. causing a pulse of laser energy to be transmitted into said liquid passing through the lumen of said catheter such that said liquid will carry said laser energy into contact with said artery surfaces, thereby causing irradiation of said artery surface; and,
 d. maintaining the pulse duration of said pulse of laser energy such that the elapsed time from the beginning of said pulse to the end of said pulse is less than the thermal relaxation time of the irradiated artery surface.

32. The method of claim 31 wherein said laser transmitting liquid comprises a radiographic contrast medium.

33. A method for delivering laser energy to a treatment site within a mammalian body through an elongate laser catheter having a hollow lumen extending therethrough, said method comprising the steps of:
 a. inserting, into said body, an elongate liquid core laser catheter having a liquid carrying lumen extending longitudinally therethrough such that a flow of laser transmitting liquid may be infused through said catheter;
 b. passing a laser transmitting liquid through the liquid carrying lumen of said catheter such that said liquid passes through said catheter and into contact with said treatment site within said body;
 c. causing a pulse of laser energy to be transmitted into said liquid passing through the lumen of said catheter such that said liquid will carry said laser energy into contact with said treatment site within said body, thereby causing irradiation of said treatment site; and,
 d. maintaining the pulse duration of said pulse of laser energy such that the elapsed time from the beginning of said pulse to the end of said pulse is less than the thermal relaxation time of the irradiated treatment site within said body.

34. The method of claim 33 wherein said laser transmitting liquid comprises a radiographic contrast medium.

35. The method of claim 33 wherein said radiographic contrast medium is selected from the group of radiographic contrast media commercially available as:
Angiovist (Berlex, Wayne, N.J.); and
Hexabrix (Mallincrodt, St. Louis, Mo.).

* * * * *